United States Patent [19]
Kontos

[11] Patent Number: 5,800,391
[45] Date of Patent: *Sep. 1, 1998

[54] ANGIOPLASTY BALLOON CATHETER AND ADAPTOR

[75] Inventor: Stavros B. Kontos, Woodcliff Lake, N.J.

[73] Assignee: Boston Scientific Corporation, Natick, Mass.

[*] Notice: The term of this patent shall not extend beyond the expiration date of Pat. No. 5,501,668.

[21] Appl. No.: 616,618

[22] Filed: Mar. 15, 1996

Related U.S. Application Data

[63] Continuation of Ser. No. 229,696, Apr. 19, 1994, Pat. No. 5,501,668, which is a continuation of Ser. No. 743,189, Aug. 9, 1991, Pat. No. 5,318,529, which is a continuation-in-part of Ser. No. 657,381, Feb. 19, 1991, abandoned, which is a continuation of Ser. No. 403,497, Sep. 6, 1989, abandoned.

[51] Int. Cl.⁶ .................................................. A61M 29/00
[52] U.S. Cl. ........................................... 604/96; 606/194
[58] Field of Search ...................... 604/96–103; 606/192, 606/194; 128/656–658

[56] References Cited

U.S. PATENT DOCUMENTS

| | | | |
|---|---|---|---|
| 4,606,347 | 8/1986 | Fogarty et al. | 128/344 |
| 4,616,653 | 10/1986 | Samson et al. | 128/344 |
| 4,684,363 | 8/1987 | Ari et al. | 604/98 |
| 4,734,093 | 3/1988 | Bonello et al. | 604/95 |
| 4,755,371 | 7/1988 | Mueller, Jr. | 604/280 |
| 4,793,350 | 12/1988 | Mar et al. | 128/344 |
| 4,877,031 | 10/1989 | Conway et al. | 128/344 |
| 4,906,241 | 3/1990 | Noddin et al. | 606/194 |
| 4,964,409 | 10/1990 | Tremulis | 128/657 |
| 4,976,720 | 12/1990 | Machold et al. | 606/194 |
| 4,998,917 | 3/1991 | Gaiser | 604/96 |
| 5,002,559 | 3/1991 | Tower | 606/194 |
| 5,032,113 | 7/1991 | Burns | 604/96 |
| 5,035,686 | 7/1991 | Crittenden et al. | 604/96 |
| 5,085,636 | 2/1992 | Burns | 604/99 |
| 5,135,487 | 8/1992 | Morrill et al. | 604/96 |
| 5,171,221 | 12/1992 | Samson | 604/96 |
| 5,176,637 | 1/1993 | Sagae | 604/96 |
| 5,195,989 | 3/1993 | Euteneuer | 604/280 |
| 5,217,434 | 6/1993 | Arney | 604/99 |
| 5,246,420 | 9/1993 | Kraus et al. | 604/95 |

FOREIGN PATENT DOCUMENTS

| | | |
|---|---|---|
| 2002767 | 5/1990 | Canada . |
| 2072584 | 6/1991 | Canada . |
| 2068483 | 11/1992 | Canada . |
| 0213752 | 3/1987 | European Pat. Off. . |
| 0368523 | 5/1990 | European Pat. Off. . |
| 0462801 | 12/1991 | European Pat. Off. . |
| 2091779 | 3/1992 | Japan . |
| 91/13649 | 9/1991 | WIPO . |
| 92/08511 | 5/1992 | WIPO . |
| 93/07925 | 4/1993 | WIPO . |
| 93/11826 | 6/1993 | WIPO . |
| 93/18816 | 9/1993 | WIPO . |

*Primary Examiner*—Corrine M. McDermott
*Attorney, Agent, or Firm*—Fish & Richardson P.C.

[57] ABSTRACT

The invention described is a single lumen balloon catheter with a detachable adaptor, a rotatable guide wire and a short guide tube, in which the guide tube provides a path for the guide wire, the adaptor incorporates means for rotating the guide wire and whereby axial force can be transmitted to the guide tube.

18 Claims, 6 Drawing Sheets

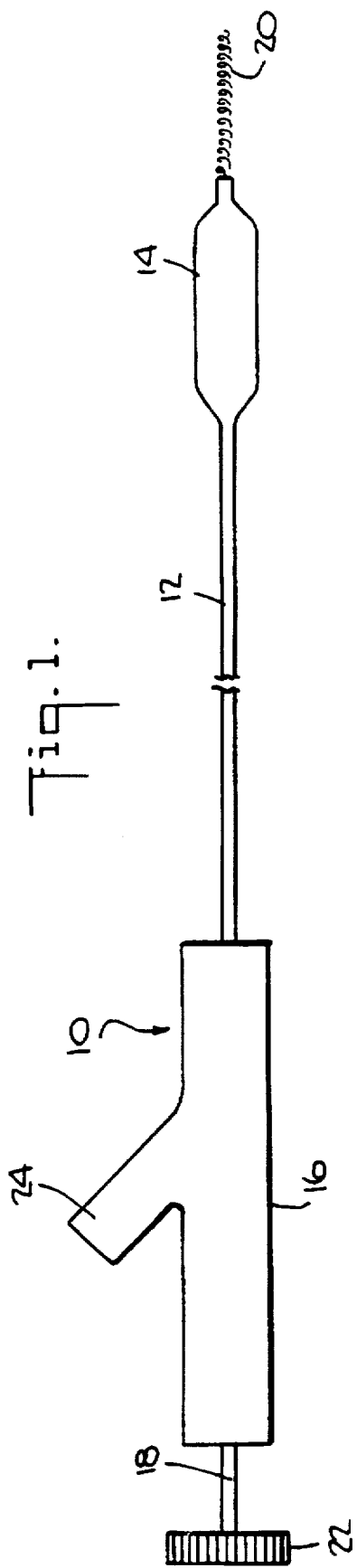
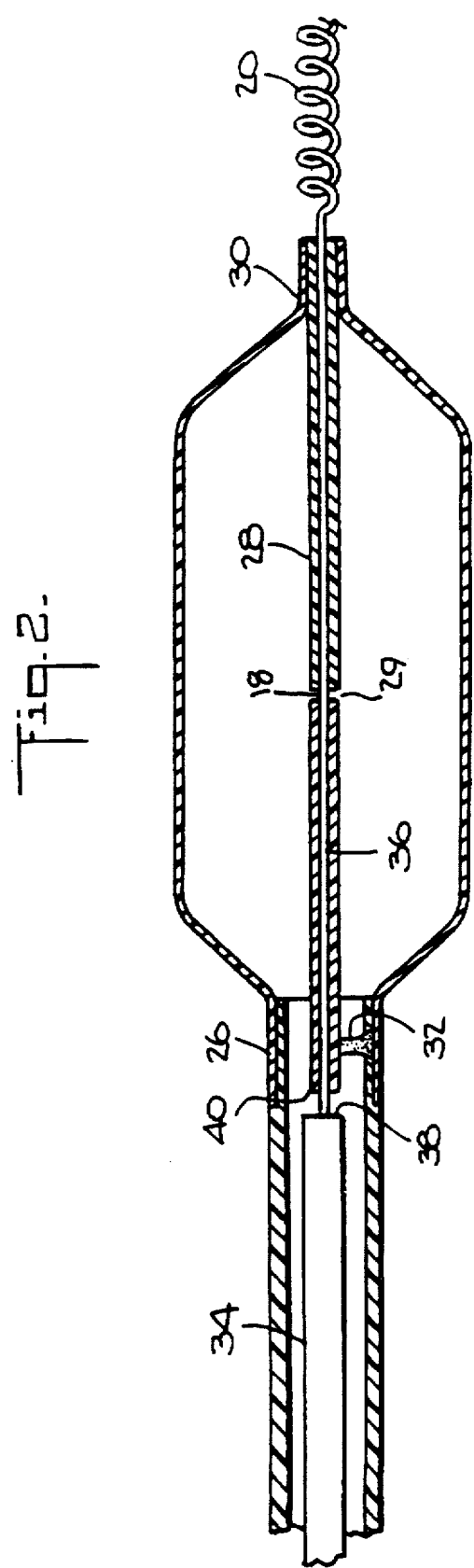

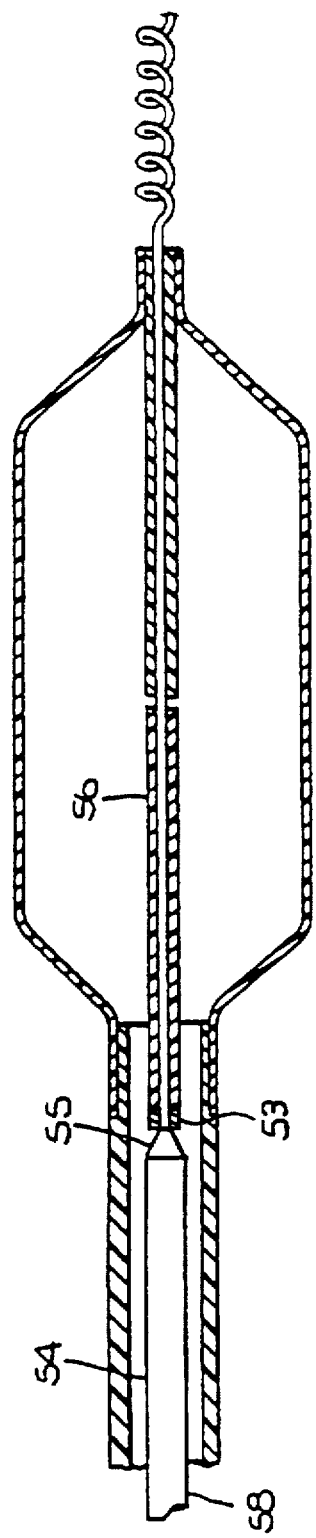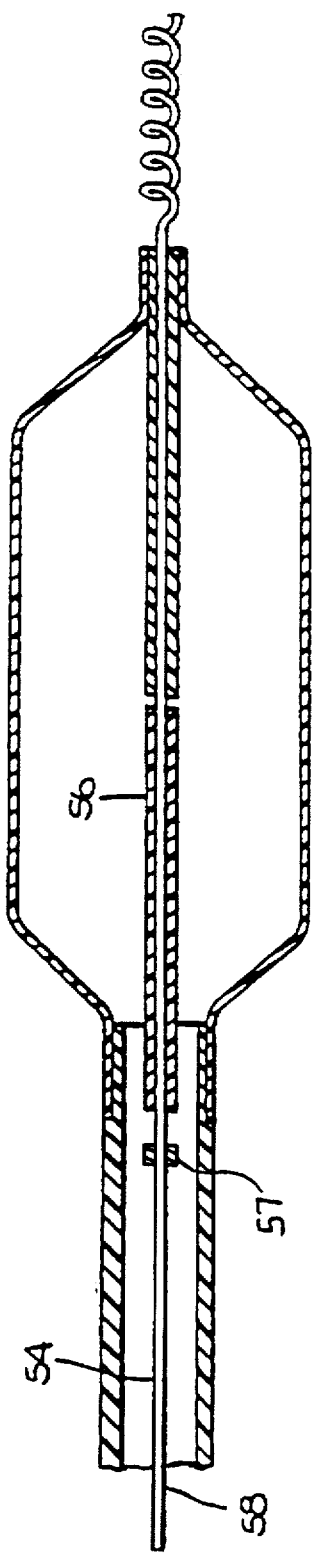

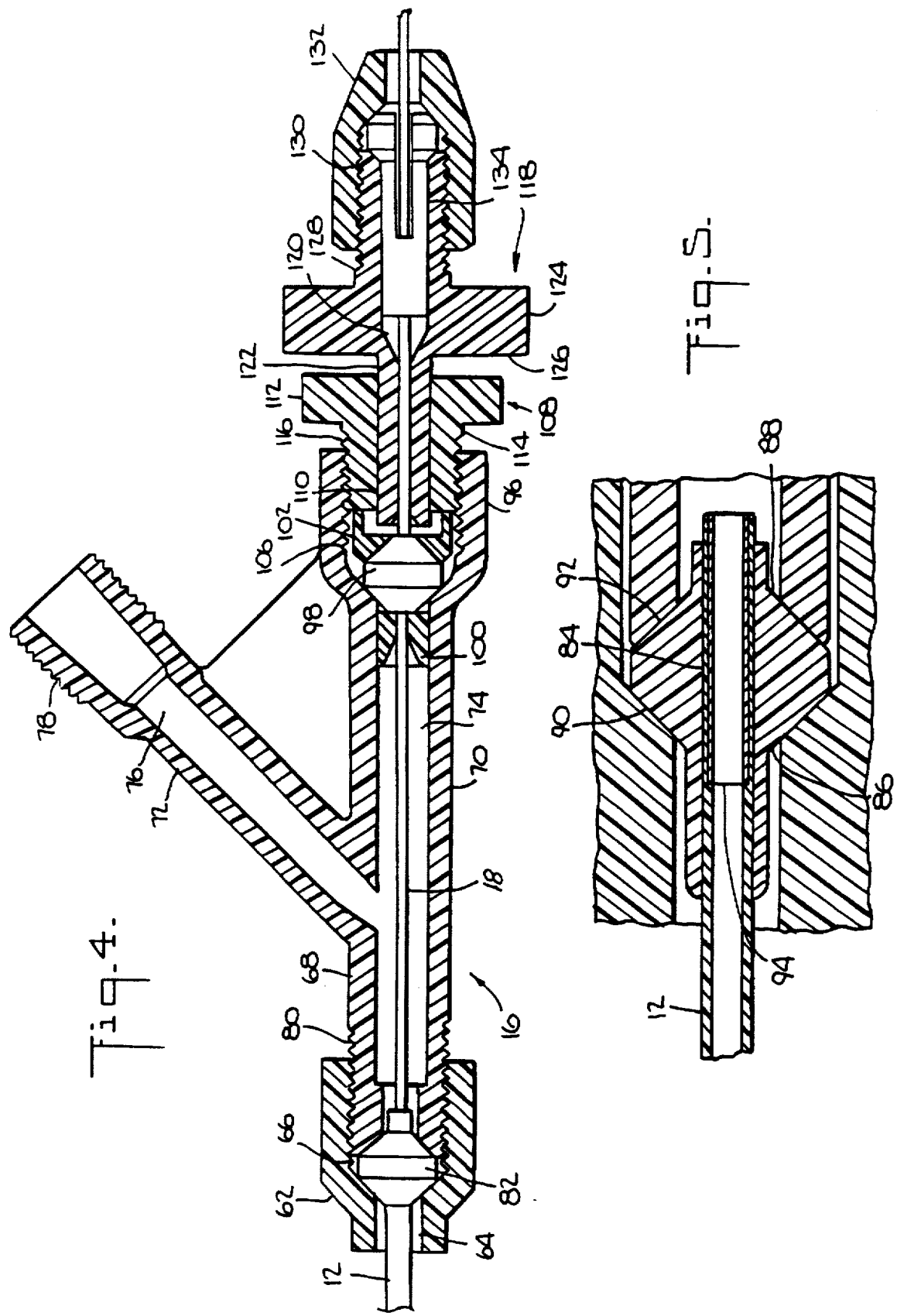

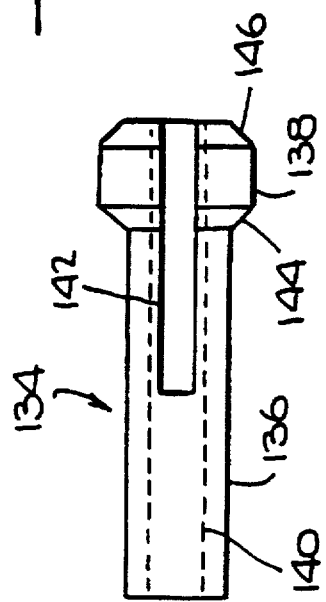
Fig. 6.
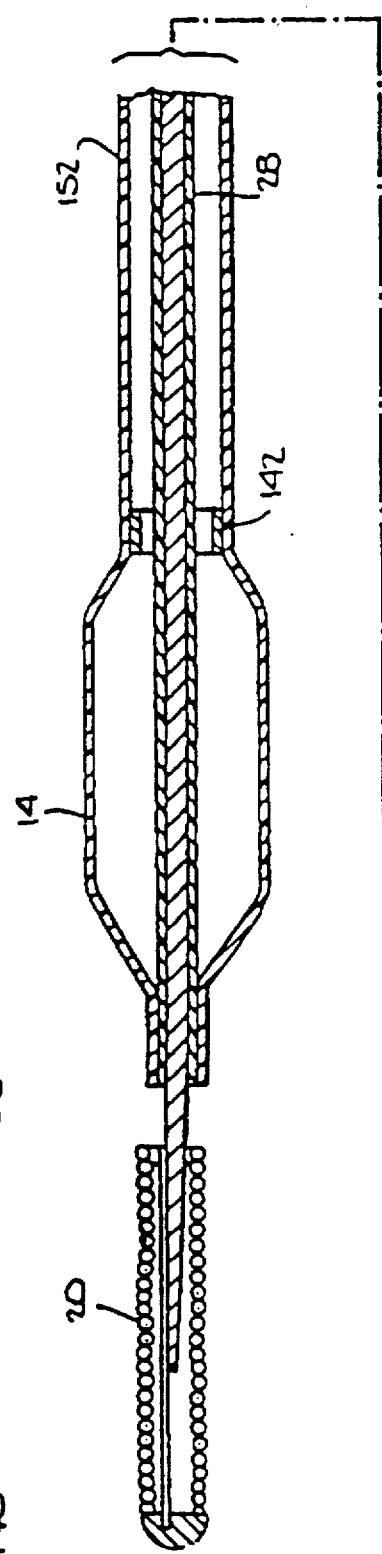
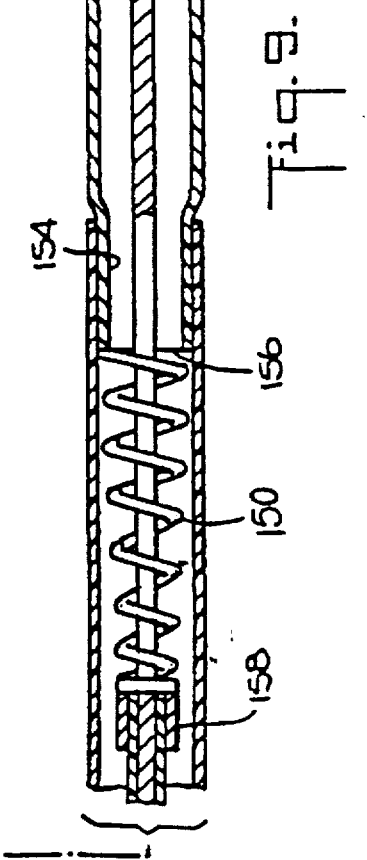
Fig. 9.

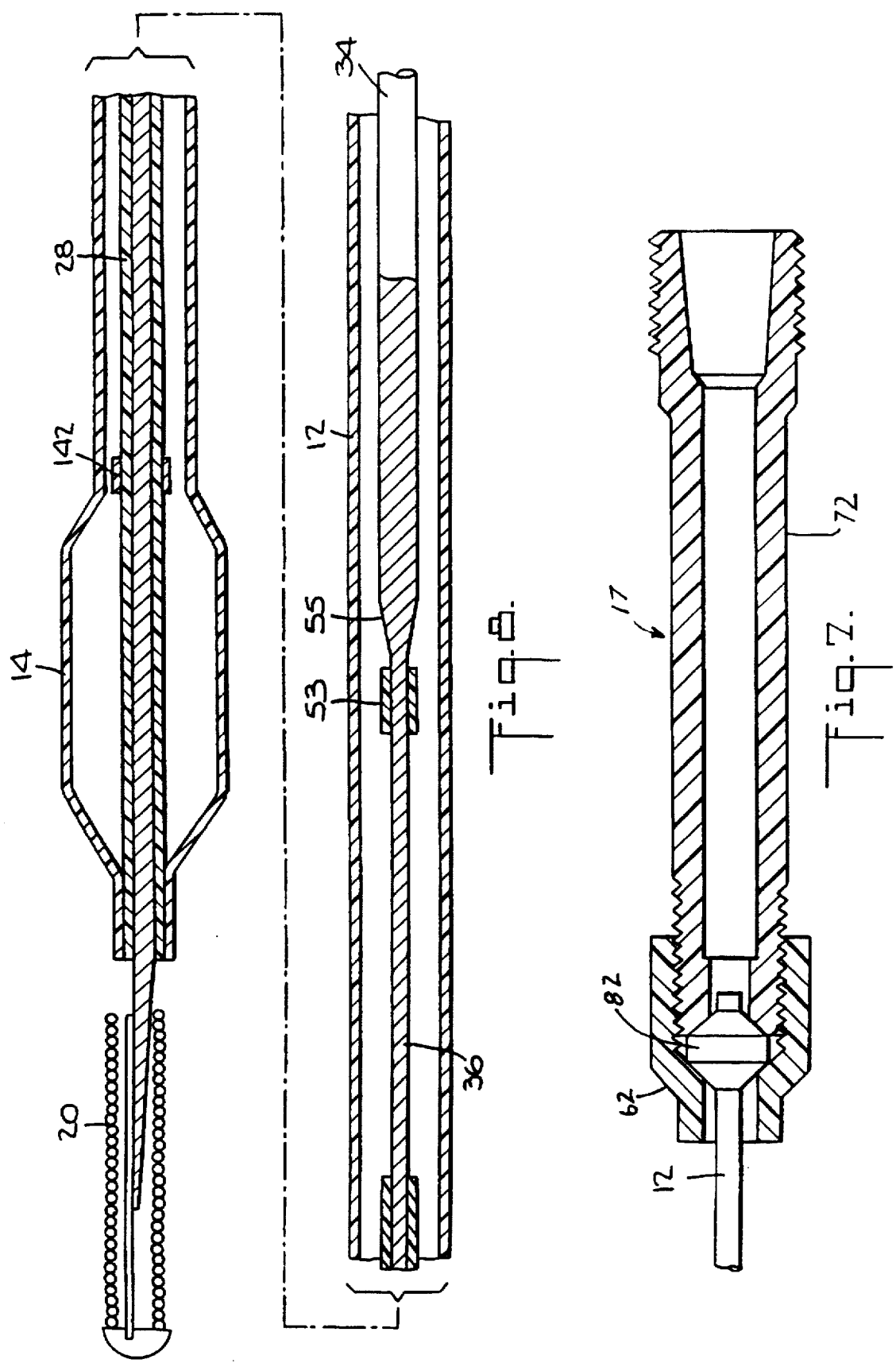

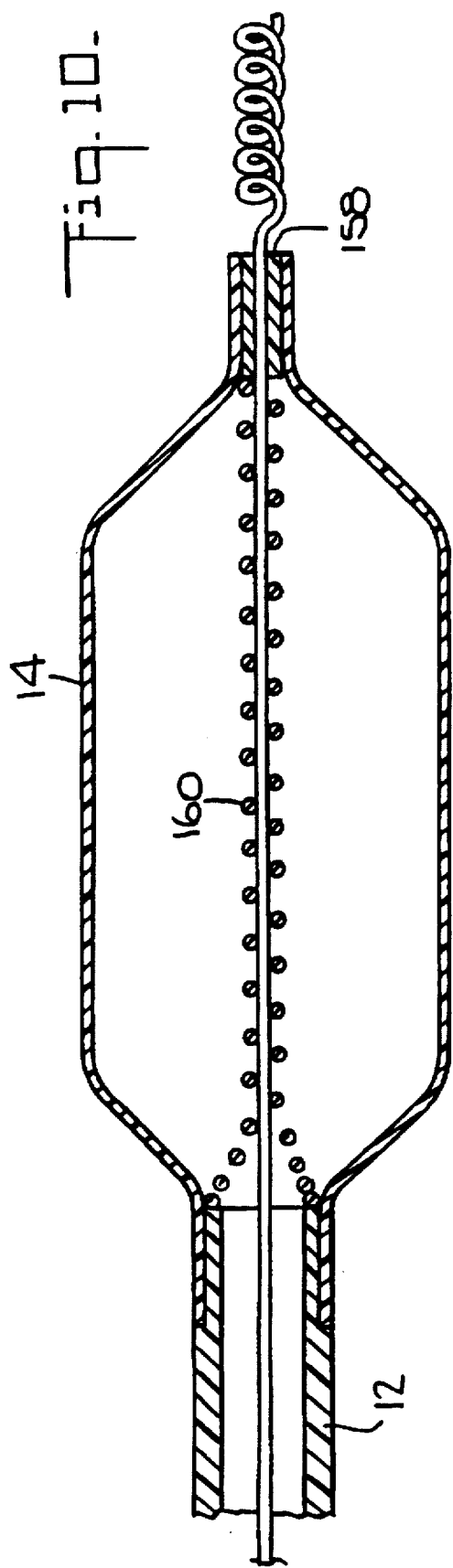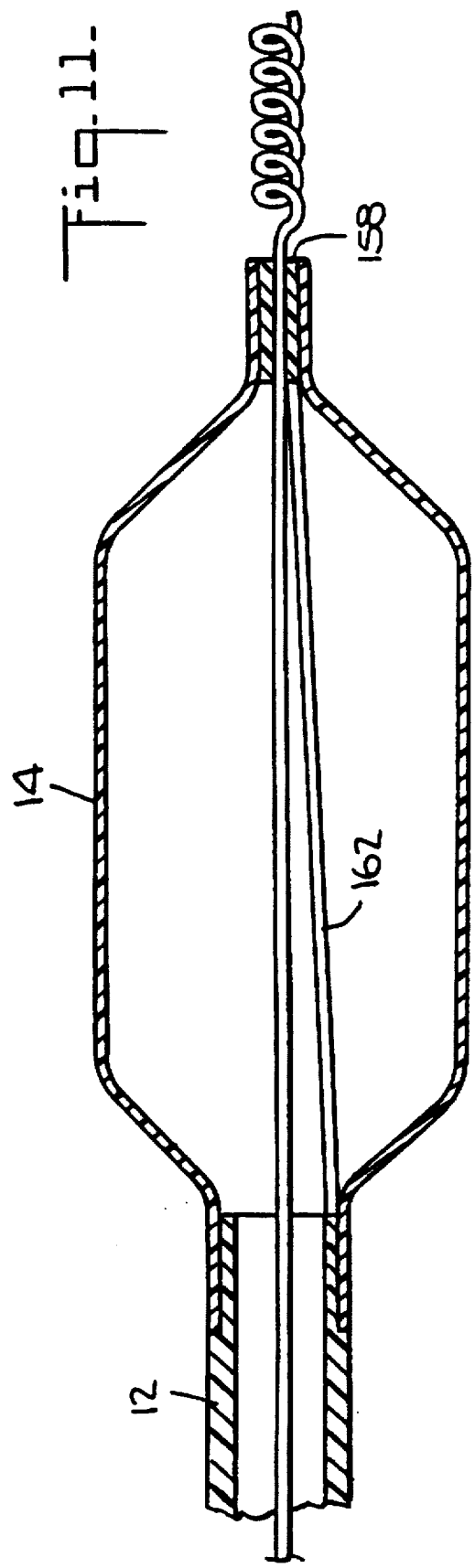

ANGIOPLASTY BALLOON CATHETER AND ADAPTOR

This is a continuation of application Ser. No. 08/229,696, filed Apr. 19, 1994, now U.S. Pat. No. 5,501,668 which is a continuation of application Ser. No. 07/743,189, filed Aug. 9, 1991, now issued U.S. Pat. No. 5,318,529, which is a continuation-in-part of application Ser. No. 07/657,381, filed Feb. 19, 1991, now abandoned, which is a continuation of application Ser. No. 07/403,497, filed Sep. 6, 1989, now abandoned.

BACKGROUND OF THE INVENTION

Angioplasty balloon catheters are well known in the art. Basically they are comprised of a balloon portion and a catheter tube portion, the balloon portion being mounted on or attached to the catheter tube portion at or adjacent the distal end thereof. In use, the balloon portion is advanced through an artery, often over a guide wire which had previously been passed through the artery. The advancement is continued until the balloon is within a stenosis. It is then expanded by application of fluid pressure through the catheter tube.

Angioplasty catheters are normally of relatively small diameter and are preferably very flexible or "soft" to facilitate negotiating often very tortuous arterial paths. The balloon is advanced through the arterial tree by pushing on the catheter tube.

Sometimes, during the advancement of the balloon through the artery, it may encounter a lesion which impedes passage. In such a case, further force applied to the catheter, instead of producing further advancement of the balloon, merely causes the tube and/or the balloon, to crinkle, or collapse, or double up on itself within the artery. Most, often, the obstruction which leads to this is the very lesion causing the stenosis which the balloon is intended to expand.

Indwelling, or in situ guide wires have been used to try and overcome this difficulty. Because they are much thinner than the catheters and since they tend to be stiffer, they can often be guided through the small lumen of a stenotic region which a catheter alone might not be able to negotiate. With the guide wire having traversed the area of the lesion, a catheter passing over that wire can then find and negotiate that same path much more easily than if the guide wire were not there. Such guide wires also help the catheters passing over them to resist buckling as they pass through severely narrowed sections of the artery. Nevertheless, they have been only partially successful in ameliorating the tendency of the very flexible catheter tube to collapse, buckle or fold upon itself. That is because the axial force necessary to advance the balloon is still transmitted through the soft, flexible catheter tube. In addition, the need to pass over an indwelling guide wire imposes a minimum size limitation upon the diameter of the catheter tube and, as a result, on the collapsed profile of the balloon section. That minimum size can still be too large to enable the balloon to enter the lesion destined for treatment.

Moreover, the thrust recently has been toward making the in situ guide wire more, not less flexible in order to enable it more easily to negotiate the tortuous path to the lesion. However, as the guide wire becomes more flexible, its ability to inhibit the collapsing or folding of the catheter tube diminishes.

Numerous attempts have been made over the years to design angioplasty catheters which are soft and flexible and yet can transmit axial forces without buckling. Among the most recent is reflected in U.S. Pat. No. 4,616,653 (Samson) which discloses a combination angioplasty catheter with a built-in guide wire. The system of the '653 patent employs a dual lumen catheter, with the inner lumen beginning at the distal end of the balloon, passing through the balloon chamber and then the full length of the catheter tube, ending at its proximal end. In addition, the inner lumen of Samson has at least three segments, a small diameter segment that passes through the balloon chamber, a larger diameter segment that passes through the catheter tube and a transition segment between the other two.

While the device of the '653 patent may overcome some of the obstacles of the prior art devices, it is believed to have its own drawbacks. The use of coaxial tubes over the entire length of the device adds unnecessary rigidity and reduced flexibility in regions where it may not be needed or desired. Also, the use of a dual diameter inner tube, and the need to provide a transition zone with a taper that will not stretch when the guide wire taper is forced into it is believed to make the device of the '653 patent unnecessarily difficult and costly to fabricate.

BRIEF DESCRIPTION OF THE PRESENT INVENTION

In accordance with one embodiment of the present invention, an angioplasty balloon catheter assembly is provided in which the guide wire, sometimes referred to merely as a safety guide, and the balloon are used in a cooperative relationship so that a force applied to the guide wire can advance the balloon through a restricted lesion area. This is accomplished by providing mechanical engagement between the guide wire and the balloon so that axial force applied to the wire from outside of the body of the patient will be transmitted to the distal end of the balloon. Further, in accordance with the invention, the distal end of the guide wire can be made highly flexible, or can be attached to a flexible coil spring, so that the guide wire can be more easily advanced through stenoses and accommodate sudden changes in direction. Also, most of the body of the catheter tube is of a single lumen design, thereby retaining the advantageous characteristics of such construction.

In one embodiment of the invention, the catheter tube runs from the extreme proximal end of the entire assembly to the proximal end of the balloon membrane, but preferably does not run through the balloon chamber to its distal end. In addition, a guide tube is provided. The guide tube can include a neck extension on the distal end of the balloon. The guide tube continues from the tip end, into and through the balloon chamber, to and preferably slightly into the catheter tube, terminating in the distal portion of the catheter tube. The outside diameter of the guide tube is smaller than the inside diameter of the catheter tube.

The guide wire extends from, and preferably through the entire length of the guide tube and the balloon chamber as well as through the catheter tube and the fitting at the proximal end of the catheter tube. It is attached at the proximal end of the catheter tube to a rotating member, such as a knob, which preferably is incorporated as part of the proximal fitting. Stop means are associated with the guide wire to interact with the proximal end of the guide tube. When force is applied to the proximal end of the guide wire, it will be transmitted along the length of the wire, to the guide tube and thence to the distal end of the balloon.

In another embodiment of the invention, the catheter tube is comprised of an extension tube and a main body, which may be, for example, of thin walled stainless steel tubing or a polyamide tube. The distal end of the main body forms a shoulder inside the extension tube and a coil spring transmits axial force from that shoulder to the guide tube. In this embodiment, the axial force is transmitted primarily through the catheter tube, rather than primarily through the guide wire.

Although it is believed that the catheter assembly structure of the instant invention is particularly well suited for angioplasty balloon catheters, it may also have utility for other types of catheters, for example, intra-aortic balloon catheters.

Another feature of the instant invention is a catheter adaptor. This adaptor can be used with a variety of different types of catheters, but is believed particularly suited for use with PTCA catheters. The adaptor can be removed and reattached, as need dictates. Also, the guide wire can be removed with or without removal of the adaptor.

BRIEF DESCRIPTION OF THE DRAWINGS

Other objects and advantages of the present invention will become more apparent upon reference to the following specification and annexed drawings in which:

FIG. 1 is an extended schematic plan view of a preferred embodiment of the invention.

FIG. 2 is a cross sectional view of the distal end portion of the embodiment of FIG. 1;

FIG. 3 is a cross sectional view of the distal end portion of another embodiment of the invention;

FIG. 3A is a cross-sectional view of the distal end portion of a balloon angioplasty catheter.

FIG. 4 is plan view of the proximal end of the catheter of an embodiment of the invention showing an adaptor and rotatable knob in cross section.

FIG. 5 is an enlarged cross sectional view of the forward compression seal region of the adaptor of FIG. 4.

FIG. 6 is a side view of a split collet used in conjunction with the adaptor of FIG. 4.

FIG. 7 is a cross sectional view of an alternative embodiment of the adaptor of FIG. 4.

FIG. 8 is a cross sectional view of the distal end portion of a catheter showing another embodiment of the instant invention.

FIG. 9 is a cross sectional view of the distal end portion of a catheter showing yet another embodiment of the instant invention.

FIG. 10 is a cross sectional view of the distal end portion of a catheter showing still another embodiment of the instant invention.

FIG. 11 is also a cross sectional view of the distal end portion of a catheter showing yet one more embodiment of the instant invention.

DETAILED DESCRIPTION OF THE INVENTION

Referring to FIG. 1, the angioplasty balloon catheter assembly 10 one embodiment of the present invention includes a catheter tube 12, a balloon membrane 14, an adaptor or fitting 16 and a captive safety guide 18. The proximal end of the catheter 12 fits into and is sealed to adaptor 16. Adaptor 16, which has a leg 24, is preferably molded or machined of an inert, biologically compatible material.

Passing through the entire balloon catheter assembly is the safety guide or guide wire 18. At its proximal end, the guide wire is provided with a rotatable knob 22 and at its distal end is a very flexible coil spring 20.

Turning to FIG. 2, it can be seen that the proximal end 26 of balloon membrane 14 is attached and sealed to the distal end of catheter 12 in conventional fashion, for example by gluing, chemical welding or the like. The distal end 30 of balloon 14 is attached and sealed, again in conventional fashion, to the distal end portion of guide tube 28. At its proximal end, guide tube 28 is attached to catheter tube 12, preferably by a few or a series of circumferentially spaced spot welds 32. In this embodiment, guide tube 28 acts not merely as a guide for the safety guide wire, but as the support member for the balloon as well. In addition, in this embodiment, at least some axial force can be transmitted directly from the catheter tube to the guide tube and thence to the distal end of the balloon.

Because guide tube 28 is attached to catheter tube 12 and because balloon membrane 14 is attached to tube 28 at one end and to tube 12 at the other, expansion of the membrane tends to stress the points of attachment at both ends. Accordingly, if one wishes to avoid such stresses, a cut 29 may be made in guide tube 28 to permit axial movement of its distal end relative to its proximal end, thereby preventing the development of stress at the points of attachment. Despite this cut, however, guide tube 28 acts as a support member for the balloon. Safety guide 18 acts as a necessary support member only to bridge the gap created by cut 29. As another alternative, a spring can be employed to bridge this gap. It should be understood, however, that stress relief means such as cut 29 are not necessary to practice the instant invention.

As can be seen in FIGS. 3 and 8, the guide tube need not be attached to catheter tube 12. Instead, it can float freely in the lumen of tube 12. When not so attached, there is even less need for stress relief cut 29 (FIG. 8), although it still may be provided.

Also, the guide tube need not be made of solid wall tubing nor need it be circular in cross section. All that is required is that a seal be established to prevent blood from entering the lumen of the catheter and/or the balloon chamber.

It is believed to be most desireable to provide for very close tolerances, perhaps on the order of 0.0005 inches, between the inside diameter of the guide tube and the outside diameter of guide wire segment 36. Such close tolerances prevent seepage of blood into the catheter tube and also prevent the balloon expansion fluid from escaping into the blood stream. Under certain circumstances, however, additional sealing means may be desireable. For example, the guide tube can be filled with a thixotropic material. Another method would be to employ an elastomeric seal.

It is believed most advantageous to provide for a tight fit between guide wire and guide tube over the entire length of the guide tube. Alternatively, a tight fit need only be assured over a portion of the guide tube's length. In the latter case, the structure and configuration of the remainder of the guide tube is largely a matter of choice.

As can also be seen in FIG. 2, the main body of safety guide 18 is comprised of two segments, a proximal segment 34 and a distal segment 36. Segment 34 is the longer of the two and has a larger diameter than that of segment 36. At its proximal end, segment 34 is attached to knob 22 and at its distal end it is attached to segment 36. Segment 36 is attached at its proximal end to segment 34, and at its distal end it is attached to or formed into a coil 20.

Between its attachment to segment 34 and coil 20, segment 36 passes through guide tube 28. Accordingly, the inside diameter of guide tube 28 must be larger than the diameter of segment 36. Obviously, the dimensions of these two cooperating elements may vary depending upon the size of the balloon being employed. However, in a typical small diameter or predilatation catheter having an expanded balloon diameter of between about 0.040 and about 0.160 inches, the guide tube might have an outside diameter of about 0.010 inches and an inside diameter of 0.007 inches, whereas the safety guide segment 36 might have a diameter of 0.007 inches and segment 34 might have a diameter of 0.013 inches.

The balloon portion of a predilatation catheter like that just referred to is generally about one inch long, with the catheter tube 12 having an inside diameter of about 0.024 inches and an outside diameter of about 0.032 inches.

Because the two segments, 34 and 36, of guide wire 18 are of differing diameters, a shoulder 38 is formed where they meet. The outside diameter of the shoulder is made larger than the inside diameter of guide tube 28. Thus, when axial force is exerted on safety guide 18, face 38 of the shoulder abuts the proximal face 40 of guide tube 28 and thereby transmits the axial force to the guide tube, and through it, to the distal end 30 of balloon 14.

Although in order to serve its mechanical support function in this embodiment, the guide tube need be only so long as to prevent its leaving the mouth of catheter 12 when balloon membrane is inflated, it may be desireable, as is seen, for example, in FIGS. 3 and 8, to extend it slightly further into catheter 12 in order to improve the seal that is created as a result of the close tolerances between the inside diameter of the guide tube and the outside diameter of the distal segment of the guide wire. It is believed, however, that the guide tube should not extend into catheter 12 for a substantial portion of the length of catheter 12. Most advantageously, the guide tube should not extend into catheter 12 for more than about 25% of the catheter's length, and preferably not more than about 10% of its length.

While safety guide 18 effectively plugs the lumen of guide tube 28, because of the innovative structural arrangement at the proximal end of tube 28, fluid communication is maintained between the lumen of catheter tube 12 and the balloon chamber. Moreover, such communication is maintained without employing a dual lumen catheter.

After exiting from the distal end of guide tube 28, safety guide segment 36 may be attached to or may itself be formed into a coil 20. The outside diameter of coil 20 can be made larger than the inside diameter of guide tube 28, in which case axial movement of safety guide 18 would be limited by shoulder face 38 in the distal direction and by coil 20 in the proximal direction.

An alternative embodiment is depicted in FIG. 3. In this embodiment the transition from proximal segment 54 to distal segment 56 of safety guide 58 is by means of a frusto-conically shaped taper 55. This transition segment could take on a wide variety of other shapes, for example, frusto-spherical, frusto-elliptical or the like. When a taper is used, a sleeve 53 may be used to prevent the taper from being jammed into the guide tube. Sleeve 53 would then also provide a bearing surface between the taper and the guide tube. It will be readily apparent to those familiar with this art that, as another alternative embodiment (FIG. 3A), both the proximal segment 54 and the distal segment 56 of safety guide 58 may be of the same diameter with a keeper or collar 57 mounted thereon to act as the stop means.

Frequently a permanent bend is placed in the coil to enable the physician to "steer" it through a tortuous path and into the proper one of numerous coronary arteries. Such "steering" is accomplished by rotation of knob 22.

As can be seen, for example in FIG. 2, the distance between the shoulder formed by face 38, and coil 20 is greater than the length of guide tube 28. This is done so as to permit varying the distance by which coil 20 leads the distal end 30 of the guide tube. Of course, the distance between coil 20 and the shoulder (or keeper, or taper, as the case may be) can be the same as the length of guide tube 28. In that event, safety guide 18 would not be able to move axially relative to balloon 14, but would still be able to rotate. As another alternative, if no coil were to be used or if the coil were used but it were to be small enough to fit through the guide tube, then there would be no restriction on its movement in the proximal direction.

It is anticipated that in the most advantageous practice of the instant invention, the diameter of the main body, or proximal segment of the safety guide will be significantly larger than that of the distal segment. During insertion and proper placement, the axial force necessary to advance the catheter assembly through the arterial tree and into the stenosis of the lesion will be transmitted in part by the catheter tube and in part by the safety guide. Since it is the proximal portion of the safety guide that will be carrying the safety guide portion of the load, the larger the diameter of that segment, the greater the force it can transmit.

At the distal end, however, it is most advantageous to have the diameter of the safety guide as small as possible. The smaller the diameter of the distal segment, the smaller can be the diameter of the guide tube running through the balloon chamber and, consequently, the smaller can be the entering profile of the collapsed balloon. When the safety guide is made to be captive, the diameter of its distal segment can be made significantly smaller than that of the smallest suitable indwelling safety wire.

By use of a captive safety guide, a cooperative relationship is established between the safety guide and the catheter tube/guide tube assembly. Reliance need not be placed on the guide wire alone to negotiate the arterial tree and pass the region of the lesion.

Similarly, sole reliance need not be placed upon the catheter tube to accomplish those tasks. Instead, each acts with and reinforces the other. In particular, since the rigidity of the assembly is greater than that of the safety guide alone, to achieve a given rigidity the diameter of the safety guide can be smaller than would be possible if the guide wire were of the indwelling type. This is especially important at the distal end where a significantly smaller safety guide can be employed without compromising the ability to negotiate, steer and pass severe restrictions.

Due to the unique structure described herein, and particularly because primary reliance is placed upon the guide tube for support of the balloon, the safety guide can be made free to rotate and/or to move axially without interfering with the ability of the balloon to be fed into and through the arterial system or with its efficient functioning once in place.

In order for safety guide 18 to transmit axial force from its proximal end to its distal end and thence to guide tube 28, knob 22 is provided. In addition, cooperating structure, as best seen in FIG. 5, is provided to permit the cooperative interaction referred to above. This structure permits axial movement of the safety guide relative to fitting 16 without interfering with the freedom of the safety guide to rotate within the fitting and within the catheter tube.

The adaptor 16 of FIG. 4 is removable from and reattachable to catheter 12. Adaptor 16 has a forward compression cap 62 at its distal end, which compression cap has a hollow passage 64 therethrough with an internal thread 66 in the proximal end of passage 64. Adaptor 16 also has a Y body midportion 68 with straight leg 70 and angled leg 72. Leg 70 has hollow passage 74 therethrough and leg 72 has hollow passage 76 therethrough. Passage 76 communicates with passage 74, and passage 74 communicates with passage 64. Passage 76 has an enlarged, frusto-conically shaped proximal portion 78 designed to accept, in fluid-tight engagement, fluid pressure generating means, such as a syringe (not shown).

Leg 70 of body 68 has an external thread 80 at its distal end which is designed to engage thread 66 on compression cap 62.

Internally of cap 62 is compression seal 82. As best seen in FIG. 5, seal 82 has a hollow passage 84 therethrough and sloping converging faces 86 and 88. Compression cap 62 has an internal shoulder 90 of the same slope as face 86 and Y body leg 70 terminates at its distal end in an internal taper 92 having the same slope as face 88. Passage 84 is designed to accept catheter 12 therein.

When compression cap 62 is threaded tightly onto Y body 68, compression seal 82 is squeezed between shoulder 90 and taper 92, which squeezing in turn forces the seal to expand inwardly against catheter tube 12 and produces a fluid-tight seal between fitting 16 and tube 12. In order to prevent tube 12 from collapsing when seal 82 is compressed against it, a steel reinforcing sleeve 94 can be placed within its lumen.

The proximal end of Y body leg 70 terminates in an enlarged segment 96 having an internal thread 106. A second compression seal 98 is placed within segment 96 between back-up plates 100 and 102. Seal 98 has a hollow passage therethrough designed to accept therein guide wire 18.

Proximal of leg 70 is compression knob 108 having a hollow passage 110 therethrough, an enlarged segment 112 and a reduced diameter segment 114. Segment 114 is provided with an external thread 116 designed to engage internal thread 106 at the proximal end of leg 70. Rotation of knob 108 relative to Y body 68 compresses seal 98 between plates 102 and 100 causing it to expand inwardly against guide wire 18 thereby forming a fluid-tight seal. However, since seal 98 is made of a deformable plastic and safety guide 18 is preferably stainless steel, a fluid-tight seal can be achieved without preventing rotation or axial movement of the safety guide within the seal.

Adaptor 16 is also provided with a torque handle 118 having hollow passage 120 therethrough. The outside diameter of the distal segment 122 of handle 118 is sized to fit slidably within passage 110. Proximal of segment 122 is rotating knob 124 having a diameter greater than that of segment 122 as well as of compression knob 108. The distal face 126 of knob 124 acts as a stop or shoulder to limit axial travel in the distal direction of handle 118 relative to compression knob 108.

The proximal end of handle 118 is provided with an external thread 128 designed to engage the internal thread 130 on rear compression cap 132. There is also provided a metal split collet 134, having a sleeve portion 136, a head portion 138, a hollow passage 140 therethrough sized to accept safety guide 18 therein and a cut 142 running axially through head portion 134 and partially through sleeve portion 136. Sleeve portion 136 is sized to fit within the proximal end of the hollow passage 120, but head portion 138 is too large to fit within that cavity. Head portion 138 is provided with external converging faces 144 and 146 designed to cooperate with similarly sloping internal faces on handle 108 and on rear compression cap 132. Rotation of cap 132 relative to handle 118 compresses head 138, thereby closing cut 142 until safety guide 18 is gripped firmly within collet 134. Because the safety guide and the collet are both made of metal, this gripping action prevents both rotational as well as axial movement between the two. Conversely, guide wire 18 can easily be adjusted simply by loosening cap 132. In addition, materials are selected for handle 118, cap 132 and collet 134 which, upon threading cap 132 tightly onto handle 118, will prevent relative motion between those three elements.

In use, safety guide 18, which extends proximally of the end of tube 12, is passed through adaptor 16, while tube 12 is fed into forward compression cap 62 and through compression seal 82. Cap 62 is than threaded tightly onto Y body 68 to grab tube 12 and prevent its removal. Compression knob 108 is then threaded tightly into the proximal end of Y body leg 70 to seal that end of leg 70 and prevent the escape of fluid therefrom. Finally, rear compression cap 132 is tightened onto handle 118 until guide wire 18 is held firmly therein.

When all three threaded engagements are tight, fluid pressure can be applied through passage 76 of leg 72, through passage 74 to the lumen of tube 12 without preventing rotation and/or axial movement of handle 118 relative to Y body 68. When it is desired to remove adaptor 16, the three threads are loosened and the entire assembly can be removed from the catheter.

While adaptor 16 has been described for use in connection with an angioplasty catheter, its utility is not nearly so limited. It can be employed with any catheter that might benefit from having a detachable/reattachable fitting. For example, it might be used at the proximal end of an intra-aortic balloon catheter.

The unique design of adaptor 16 offers the physician a degree of flexibility heretofore unheard of. For example, it permits removal of the guide wire from the catheter without removing the fitting. This can be accomplished simply by unscrewing compression knob 108 from enlarged segment 96 of leg 70 and loosening compression cap 132 so as to release the grip of collet 134. After the guide wire has been removed, compression knob 108 can be replaced by a solid cap (not shown). Screwing such a cap into enlarged segment 96 would maintain a fluid tight seal at the proximal end of the adaptor.

Similarly, by keeping compression knob 108 and compression cap 132 tight while loosening only compression cap 62, the adaptor and the guide wire can be removed together, leaving only the catheter tube in place. Or, by loosening all three compression members, adaptor 16 can be removed without disturbing either the guide wire or the catheter tube.

As those skilled in the art will readily see, numerous variations on the basic design of the adaptor can easily be made. For example, additional legs similar to leg 72 could easily be provided. Another example of a variation is depicted in FIG. 7 which shows a detachable/reattachable adaptor 17 designed for use without a guide wire. As can be seen, in the embodiment of FIG. 7, straight leg 70 of FIG. 4 and all its associated fittings and components have been eliminated. In addition, leg 72, which in FIG. 4 was at an angle, is straight in FIG. 7.

In the embodiment of FIG. 7, the components having like numbers to those in the FIGS. 4 and 5 embodiment function in the same manner as has already been described in connection with those other figures. For example, compression cap 62, compression seal 82, reinforcing sleeve 94 and body 68 cooperate to hold and release catheter 12 in the FIG. 7 configuration just as they do in the configuration of FIG. 4.

In another embodiment, depicted in FIG. 9, catheter 12 is necked down at its distal end 154. There is also provided a catheter extension tube 152, the proximal end of which fits over the necked down portion 154 of catheter 12. Preferably, the outside diameter of extension 152 should be smaller than the outside diameter of the main body of catheter 12, and a fluid tight seal should be established between the extension and the catheter. This seal can be established by any conventional means suitable to the materials being employed. When adopting this embodiment, it is believed most advantageous that catheter 12 be of thin walled stainless steel tubing and extension 152 be of modified PET. However, other biocompatible materials may also be suitable.

In the embodiment of FIG. 9, guide tube 28 extends into catheter extension 152, but stops short of the distal end of catheter 12. Between the proximal end of guide tube 28 and the distal end of catheter 12, there is provided a coil spring 150. As can be seen, the necked down end of catheter 12 forms a shoulder 156 inside catheter extension 152. At its proximal end, spring 150 abuts this shoulder 156 and at its distal end spring 150 abuts the proximal end of guide tube 28. A cap 158 may be provided over the proximal end of guide tube 28 to facilitate the even distribution of force transmitted from spring 150 to tube 28 and to reinforce the end of tube 28.

A radiopaque marker 142 is provided on the embodiments of FIGS. 8 and 9 and can be used by the physician viewing the procedure under fluoroscopy to determine where the balloon membrane begins. Similar radiopaque markers would probably be desireable on any of the embodiments of the instant invention. Practice of this invention, however, does not depend upon the use of radiopaque markers.

Although it is believed preferable to have an extended guide tube to insure a proper seal, it may also be possible for the guide tube to be short, as is depicted at 158 in FIGS. 10 and 11. In these figures the catheter 12 extends to the proximal end of balloon 14 similar to the structure depicted in FIGS. 2 and 3. In FIG. 10, however, axial force is transmitted to guide tube 158 through spring 160, whereas in FIG. 11 wire 162 serves this purpose.

In using the device of the instant invention, access to the lumen of a suitable artery, usually the femoral artery, is achieved in conventional fashion. The balloon catheter is then inserted into the artery and fed through the arterial tree, again, all in conventional fashion. Initially, and until an obstruction is reached, the balloon can be advanced simply by pushing on the catheter tube.

As the physician exerts axial force on catheter 12, in the embodiments of FIGS. 2 and 3, that axial force is transferred to the safety guide 18 through fitting 16. Because of the close fit between distal segment 36 of guide wire 18 and guide tube 28, friction will cause the transfer of that axial force to the guide tube and thence to the distal end of the balloon membrane. In the embodiment of FIG. 8, these frictional forces may be assisted or even supplanted by the transfer of force from catheter tube 12 through coil spring 150 to the proximal end of guide tube 28. In this embodiment, since reliance is not placed upon the guide wire to transmit axial force, the guide wire can be dispensed with. Alternatively, it can be made removable. As another alternative, the catheter could readily be adapted to pass over an indwelling guide wire.

When an obstruction is encountered, either due to tortuosity or stenosis or otherwise, rotating knob 22 can be used to steer the distal tip of guide wire 18 around it. Also, axial force can be applied to knob 22 to facilitate feeding of the balloon past the obstruction. Feeding of the balloon through the arterial system can continue by pushing on tube 12 and/or on fitting 16 simultaneously, thereby causing the transmission of axial forces to be shared by the catheter tube and the safety guide.

Under certain circumstances, for example, severe tortuosity or stenosis, friction alone may not be sufficient to overcome the resistance encountered. In that case, the guide tube will begin to slide axially in the proximal direction relative to catheter 12 until it encounters shoulder 38 (in the embodiment of FIG. 2) or taper 55 (of the embodiment of FIGS. 3 and 8). Alternatively, means could be provided anywhere along distal segment 36 to prevent or restrict axial movement of that segment relative to the guide tube. For example, a retaining ring (not shown) could be affixed to segment 36 and a cooperating annular cut-out provided on the inside of guide tube 28. If the length of the annular cut-out were greater than the thickness of the retaining ring, there would be leeway for a limited amount of relative axial movement. If the two were about the same size, substantially no relative motion could occur.

Although it is believed that the most advantageous means for practicing the subject invention is to employ a single adaptor, that is not a necessary attribute. The safety guide can be made to exit the catheter tube before the latter enters the adaptor. In that event, a second adaptor would be provided solely for the safety guide, with the first adaptor acting merely as the interface for connecting the catheter tube to the source of fluid pressure.

It is believed apparent from the foregoing that in the instant invention there is provided a significant step forward in the design of PTCA catheters. As will be equally apparent, the description set out above and the embodiments disclosed are necessarily only illustrative. Numerous changes, modifications and variations will readily occur to those familiar with this art and as such they should be deemed to fall within the broad scope of this invention as that scope is defined in the following claims.

I claim:

1. A fixed-wire balloon angioplasty catheter comprising:
    a main catheter body having proximal and distal ends and defining a lumen therein;
    an angioplasty balloon having proximal and distal ends and defining a balloon chamber therein, wherein the proximal end of the balloon is fixedly coupled to the distal end of the main catheter body;
    an inner tube having proximal and distal ends and defining a lumen therein, the distal end of the inner tube being fixedly coupled to the distal end of the balloon, the inner tube having an outer diameter that is smaller than the diameter of the lumen defined in the main catheter body and having a length that is substantially shorter than the length of the main catheter body;
    a captive core wire that extends from the proximal end of the main catheter body, through the lumen defined by the main catheter body, through the lumen defined by the inner tube, and terminating distally of the distal end of the inner tube and the distal end of the balloon, wherein the outer diameter of the core wire is sized with respect to the diameter of the lumen of the inner tube to provide a fluid seal therebetween;
    a steering member coupled to the distal end of the core wire and having an outer diameter that is larger than the lumen defined by the inner tube at distal end of the inner tube; and a stop positioned on the core wire at a location within the main catheter body that is proximal of the proximal end of the inner tube, the stop having a diameter that is larger than the diameter of the lumen defined by the inner tube at the proximal end of the inner tube.

2. The catheter of claim 1 wherein the clearance between the diameter of the lumen of the inner tube and the outer diameter of the core wire is on the order of about 0.0005 inches, at least in the vicinity of the distal end of the balloon.

3. A fixed-wire balloon angioplasty catheter comprising:

a main catheter body having proximal and distal ends and defining a lumen therein;

an angioplasty balloon having proximal and distal ends and defining a balloon chamber therein, wherein the proximal end of the balloon is fixedly coupled to the distal end of the main catheter body;

an inner tube having proximal and distal ends and defining a lumen therein, the distal end of the inner tube being fixedly coupled to the distal end of the balloon, the inner tube having an outer diameter that is smaller than the diameter of the lumen defined in the main catheter body and having a length that is substantially shorter than the length of the main catheter body, wherein the inner tube extends a distance proximally from the distal end of the balloon so that the proximal end of the inner tube is disposed within the lumen defined by the main catheter body;

a captive core wire having proximal and distal ends and extending from the proximal end of the main catheter body, through the lumen defined by the main catheter body, through the lumen defined by the inner tube, and terminating distally of the distal end of the inner tube and the distal end of the balloon;

a steering member coupled to the distal end of the core wire and having an outer diameter that is larger than the lumen defined by the inner tube at the distal end of the inner tube; and a stop positioned on the core wire at a location within the main catheter body that is proximal of the proximal end of the inner tube, the stop having a diameter that is larger than the diameter of the lumen defined by the inner tube at the proximal end of the inner tube.

4. The catheter of claim 3 wherein said core wire tapers from larger diameter proximal end to smaller diameter distal end.

5. The catheter of claim 3 wherein the diameter of the lumen of the inner tube is sized with respect to the outer diameter of the core wire to provide a fluid seal therebetween.

6. The catheter of claim 5 wherein the clearance between the diameter of the lumen of the inner tube and the outer diameter of the core wire is on the order of about 0.0005 inches, at least in the vicinity of the distal end of the balloon.

7. The catheter of claim 3 wherein the lumen of the inner tube has a uniform diameter.

8. The catheter of claim 3 wherein the core wire tapers from a larger diameter proximal portion to a smaller diameter distal portion, the distal portion of the core wire having a uniform outer diameter at least along the length of the core wire that extends through the lumen of the inner tube.

9. The catheter of claim 3 wherein the stop comprises a collar disposed about the circumference of the core wire at a location proximal of the proximal end of the inner tube.

10. The catheter of claim 3 wherein the core wire tapers from a larger diameter proximal portion to a smaller diameter distal portion and the stop comprises a conically tapered transition region between the larger and smaller portions of the core wire.

11. The catheter of claim 3 wherein the distance between steering member and stop is longer than length of inner tube.

12. The catheter of claim 3 wherein the steering member is a spring coil.

13. The catheter of claim 3 wherein the core member is axially movable with respect inner tube.

14. The catheter of claim 3 wherein the main catheter body is formed from a proximal tube that has a distal end and a distal tube that has a proximal end that fixedly coupled to the distal end of the proximal tube.

15. The catheter of claim 14 wherein the proximal and distal tube are made of different materials.

16. The catheter of claim 15 wherein the proximal tube is made of stainless steel and the distal tube is made of polymeric material.

17. The catheter of claim 3 wherein the balloon is bonded by adhesive to the distal end of inner tube.

18. The catheter of claim 3 further comprising a Y-adapter attached to proximal end of the main catheter body.

* * * * *